United States Patent [19]

Wasserman

[11] Patent Number: 5,060,065
[45] Date of Patent: Oct. 22, 1991

[54] APPARATUS AND METHOD FOR ILLUMINATING A PRINTED CIRCUIT BOARD FOR INSPECTION

[75] Inventor: Harold Wasserman, Belle Mead, N.J.
[73] Assignee: Cimflex Teknowledge Corporation, Princeton, N.J.
[21] Appl. No.: 483,882
[22] Filed: Feb. 23, 1990
[51] Int. Cl.⁵ .............................................. H04N 7/18
[52] U.S. Cl. .................... 358/106; 358/101; 358/107; 382/8
[58] Field of Search ............... 358/106, 101, 107; 382/8; 250/561; 356/394, 375

[56] References Cited

U.S. PATENT DOCUMENTS

| | | | |
|---|---|---|---|
| 3,916,439 | 10/1975 | Lloyd | 358/106 |
| 4,500,202 | 2/1985 | Smyth | 382/8 |
| 4,604,648 | 8/1986 | Kley | 358/101 |
| 4,677,473 | 6/1987 | Okamoto | 358/106 |

Primary Examiner—Howard W. Britton
Assistant Examiner—Sherrie Hsia
Attorney, Agent, or Firm—Weiser & Stapler

[57] ABSTRACT

A printed circuit board inspection device includes a lighting system for use with the series of cameras associated with the printed circuit board inspection device which is essentially domed in configuration, and which incorporates a plurality of selectively controllable light emitting diodes for developing desired lighting patterns. The light emitting diodes are arranged within the domed fixture to form an array of defined latitudes and longitudes, and are capable of selective activation to develop the particular lighting patterns which are desired. This permits an acquisition of images useful in developing a "topographical display" of the acquired image, which is useful in enhancing the subsequent inspections which are to be performed.

36 Claims, 5 Drawing Sheets

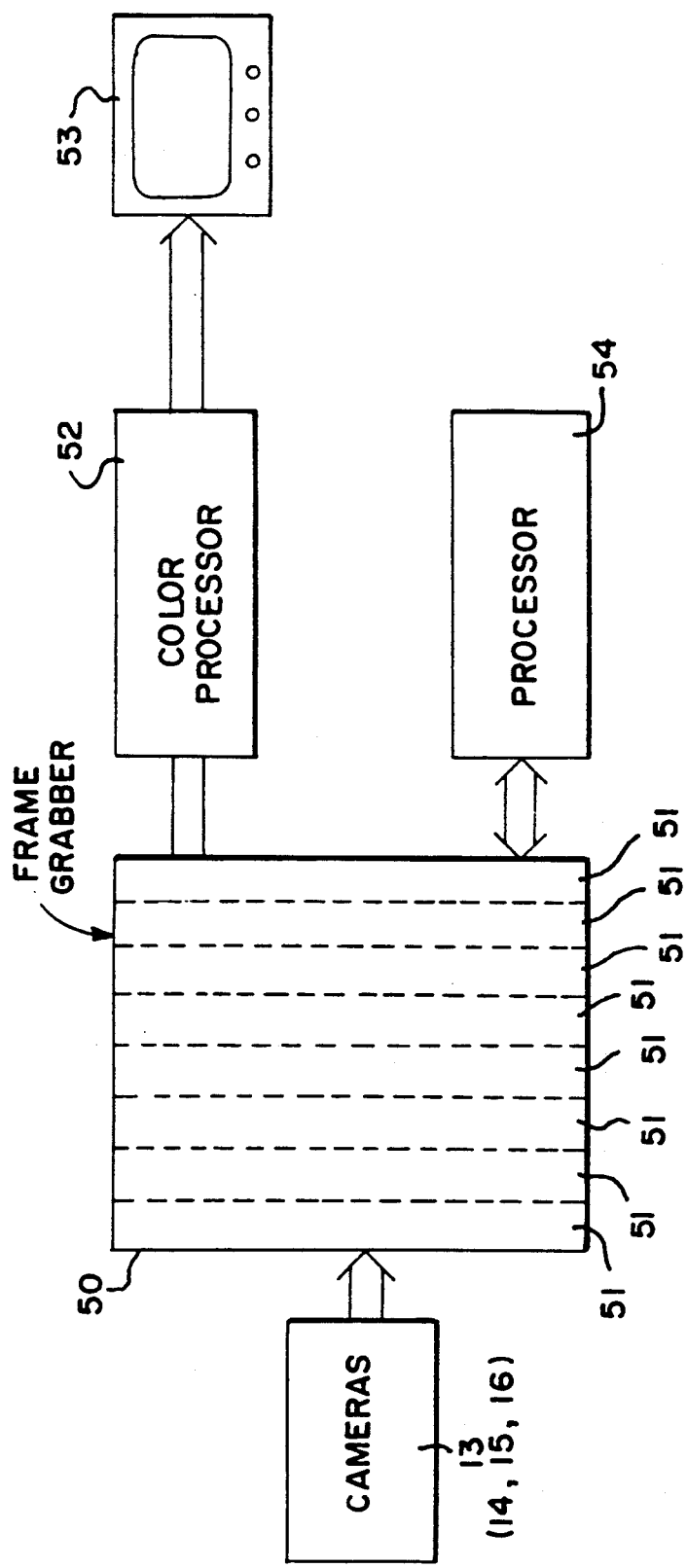

APPARATUS AND METHOD FOR ILLUMINATING A PRINTED CIRCUIT BOARD FOR INSPECTION

BACKGROUND OF THE INVENTION

This invention relates generally to systems for inspecting printed circuit boards, and more particularly, to improved illumination and processing techniques for use in conjunction with systems of this general type.

As is well known to persons skilled in the art, a printed circuit board is used for mounting and electrically interconnecting electrical components in a predetermined manner. To the extent possible, such printed circuit boards are constructed mechanically, using automated assembly machines which operate to reduce the often prohibitive costs of manually assembling a printed circuit board. While reducing overall costs, such automated assembly techniques have been found to give rise to a certain limited degree of assembly defects such as mis-insertions of components, and their leads or pins, as well as defects in the soldering procedures which would then follow.

Originally, steps were taken to locate assembly errors of this general type through a visual inspection of each printed circuit board at a desired stage of the manufacturing process, by human operators using the naked eye, or possibly a stereo microscope or the like. However, since this procedure was found to be extremely tedious and inaccurate, as well as a relatively expensive process, steps were taken to develop automated systems for inspecting printed circuit boards, to replace such visual inspections.

Examples of devices of this general type are the Model 5511 and Model 5512 Printed Circuit Board Inspection Systems which are manufactured by Cimflex Teknowledge Corporation of Princeton, N.J. These inspection devices generally employ a series of cameras which are mounted within a fixture (an inspection head) adapted for controlled movement relative to a printed circuit board. The inspection head is either sequentially advanced to successive viewing fields (typically 1 inch by 1 inch) established along the surface of the printed circuit board then under inspection, or continuously advanced along the surface of the printed circuit board, to acquire images for microprocessor analysis. Any detected defects are in turn reported to the operator, for appropriate correction.

Further detail regarding the techniques which are used to perform these inspections are disclosed in U.S. patent application Ser. No. 07/159,774, entitled "Apparatus for Inspecting Printed Circuit Boards with Surface Mounted Components", the subject matter of which is incorporated by reference as if fully set forth herein. As disclosed, the accuracy of the inspection process can be enhanced by providing an inspection head which incorporates a series of four angled, orthogonally placed cameras, operated in conjunction with a selectively controllable light source. Through selective control the series of cameras, a variety of testing procedures are enabled including a verification of the placement of components (and their leads or pins), both before and after the soldering procedure, as well as a verification of the solder connections which are made.

Previously, this was accomplished by selectively activating one of eight lighting groups provided in a generally cylindrical fixture surrounding the series of cameras used to acquire images for inspection purposes. While adequate for its intended purpose, such illumination was found to be somewhat limiting in the patterns of light which could be developed. Essentially, this was limited to the availability of either a "high" lighting group or a "low" lighting group for each of the four cameras associated with the system's inspection head.

Thus, while such lighting was found to be effective in illuminating the printed circuit board to obtain the information needed to make a proper inspection of its condition, it nevertheless became desirable to develop a more versatile lighting system for use in performing such inspections.

SUMMARY OF THE INVENTION

It is therefore the primary object of the present invention to provide an improved lighting system for a printed circuit board inspection device.

It is also an object of the present invention to provide a lighting system for a printed circuit board inspection device which provides increased versatility in selectively illuminating the regions which are to be inspected.

It is also an object of the present invention to provide a lighting system for a printed circuit board inspection device which is addressable, and more versatile in control.

It is also an object of the present invention to provide a lighting system having the above capabilities, and which is well adapted to existing printed circuit board inspection devices.

It is also an object of the present invention to provide improvements in the processing of signals acquired by the video cameras of the printed circuit board inspection device making use of the improved lighting system of the present invention.

These and other objects are achieved in accordance with the present invention by providing a lighting system for use with the series of cameras associated with the printed circuit board inspection device which is essentially domed in configuration, and which incorporates a plurality of selectively controllable light emitting diodes for developing the lighting patterns which are desired.

Further in accordance with the present invention, the light emitting diodes are arranged within the domed fixture in an array which operates to establish defined latitudes and longitudes, for selective activation as desired. This is accomplished by interconnecting the light emitting diodes in an array which constitutes what is essentially a diode control matrix, which permits the light emitting diodes to be selectively addressed to develop the particular lighting patterns which are desired.

In addition to providing the lighting patterns which are useful in performing inspections of printed circuit boards such as are described in U.S. patent application Ser. No. 07/159,774 (referenced above), the improved lighting system of the present invention has been found to permit an acquisition of images useful in developing a "topographical display" of the acquired image, which is useful in enhancing the subsequent inspections which are to be performed.

For further detail regarding the improved lighting system of the present invention, and its use in inspecting printed circuit boards, reference is made to the detailed description which is provided below, taken in conjunction with the following illustrations.

BRIEF DESCRIPTION OF THE DRAWINGS

FIG. 5 is a block diagram illustrating subsequent processing of the images which are acquired making use of the lighting system shown in FIG. 2.

In the several views provided, like reference numbers denote similar structure.

DETAILED DESCRIPTION OF THE PREFERRED EMBODIMENT

Figure 1:
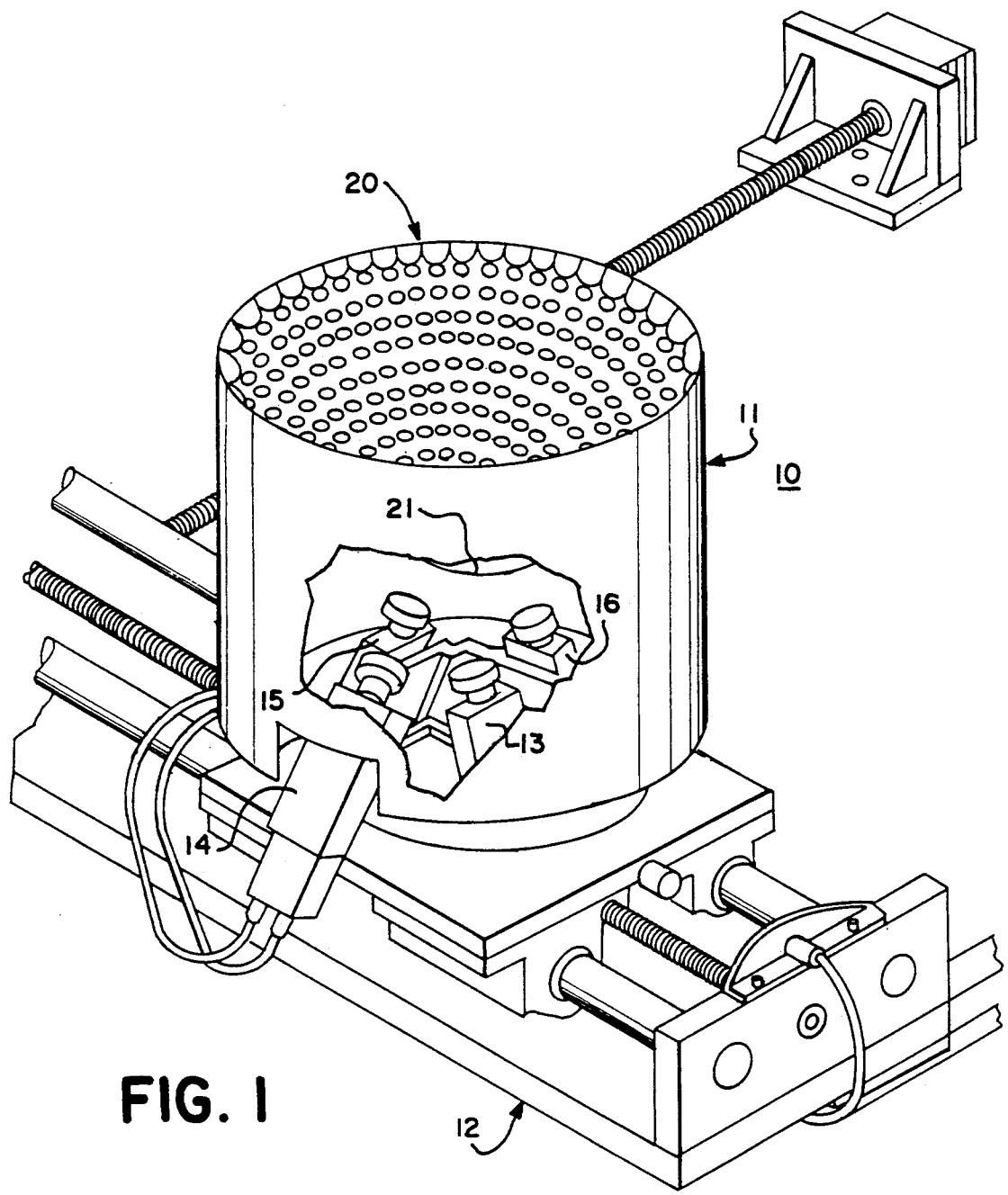
FIG. 1 is an isometric view of the inspection head of a printed circuit board inspection device, which incorporates the improved lighting system of the present invention.

FIG. 1 generally illustrates an apparatus 10 for inspecting printed circuit boards in accordance with the present invention. The apparatus 10 generally includes an inspection head 11 which is supported for predetermined movement in a defined plane by an X-Y table (generally designated by the reference number 13), using any of a variety of known servo-motor controls. Further detail regarding the basic construction of the inspection head 11 and the manner in which the inspection head 11 is caused to proceed across a printed circuit board to inspect its condition and provide an indication of potential defects may be had with reference to U.S. patent application Ser. No. 07/159,774.

Figure 2:
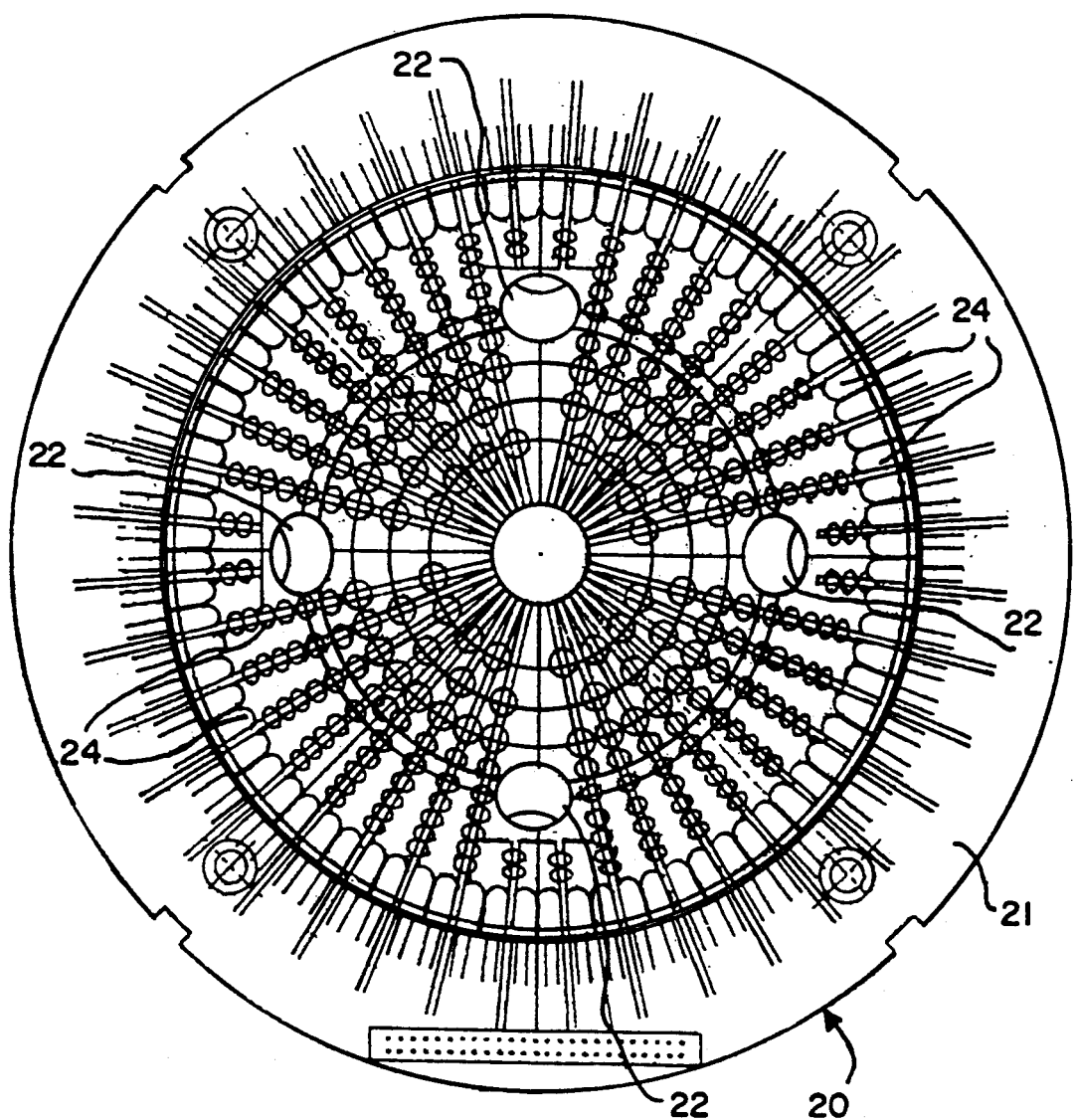
FIG. 2 is a plan view of the lighting system of the present invention, also showing the cameras which are used to acquire images for the inspection of a printed circuit board.

However, by way of general description, and referring also to FIG. 2 of the drawings, it is seen that the inspection head 11 generally includes a plurality of TV or video cameras 13, 14, 15, 16, and a lighting fixture 20 produced in accordance with the present invention. It should be understood that to this point, with the exception of the lighting fixture 20, the components previously described and illustrated in FIG. 1 essentially correspond to known components used in previously available printed circuit board inspection systems of this general type. For this reason, further discussion of the improvements of the present invention will proceed with a discussion of the improved lighting fixture 20 of the present invention, and the manner in which the lighting fixture 20 may be used to provide an enhanced inspection of printed circuit boards in accordance with the present invention.

Figure 3:
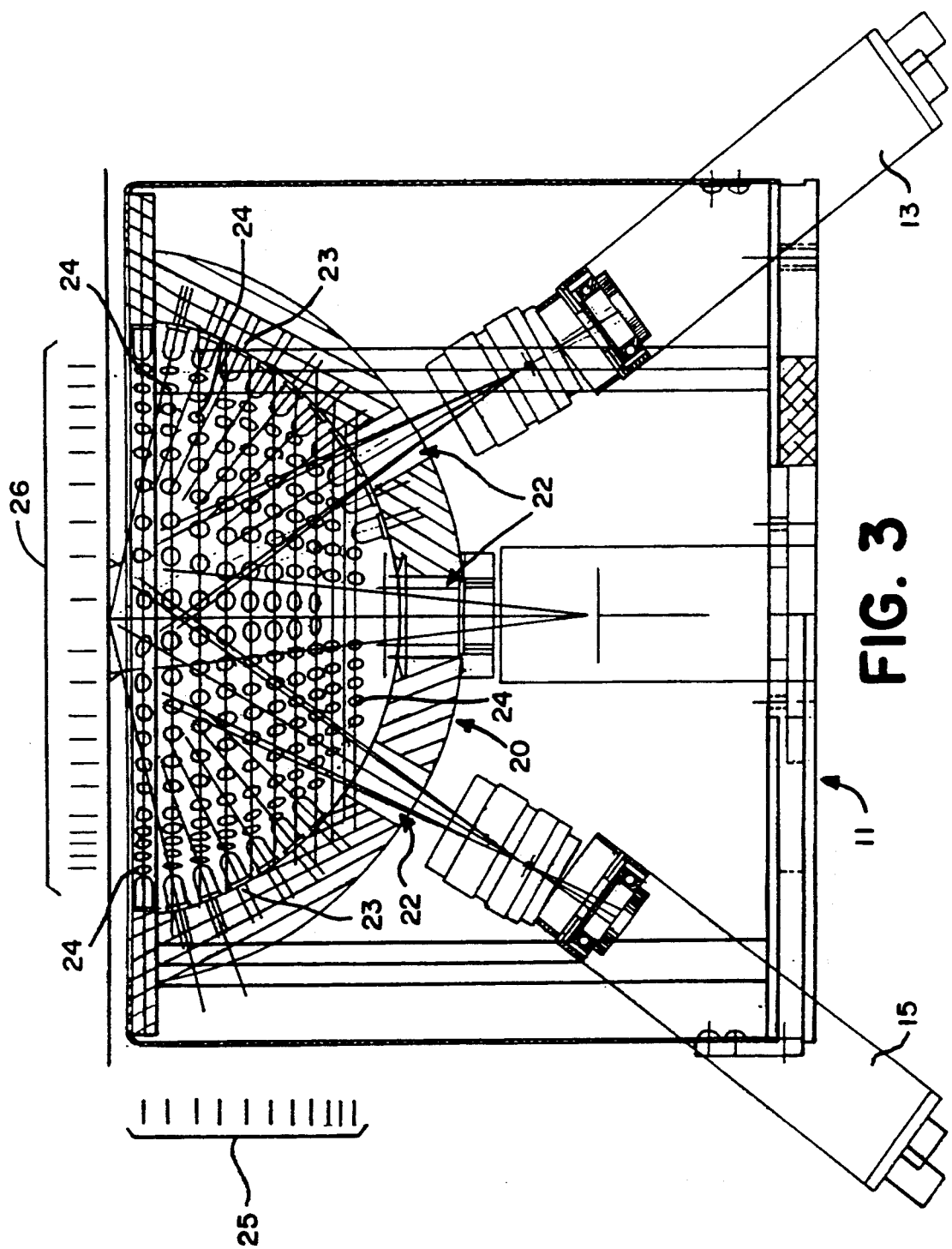
FIG. 3 is a side elevational view of the lighting system shown in FIG. 2.

Referring now to FIGS. 2 and 3 of the drawings, it will be noted that the lighting fixture 20 generally takes the form of a domed-shaped frame 21 which surrounds and depends from the series of cameras 13, 14, 15, 16. To this end, the frame 21 is provided with a series of apertures 22 for appropriately receiving the objectives of the cameras 13, 14, 15, 16. The frame 21 further incorporates a series of apertures 23 for receiving an array of light emitting diodes 24 (LED's) for illuminating a printed circuit board to be inspected by the apparatus 10. For purposes which will be explained more fully below, the series of LED's 24 are preferably disposed within the frame 21 of the lighting fixture 20 in a regular pattern which establishes a series of latitudes 25 and longitudes 26. The spacings developed between the several latitudes 25 and longitudes 26 may be varied, as desired, to achieve the lighting which is desired for a proper inspection of a printed circuit board in accordance with the present invention.

An important aspect of the lighting fixture 20 of the present invention is its use of LED's 24 for purposes of illuminating the printed circuit board under inspection. This arises from the "dual function" of a light emitting diode, that being its ability to be "strobed" to provide the lighting which is desired, as well as its "directional" operation. This dual functionality operates to provide an easily controlled lighting system which can effectively illuminate a desired area (i.e., viewing field).

Figure 4:
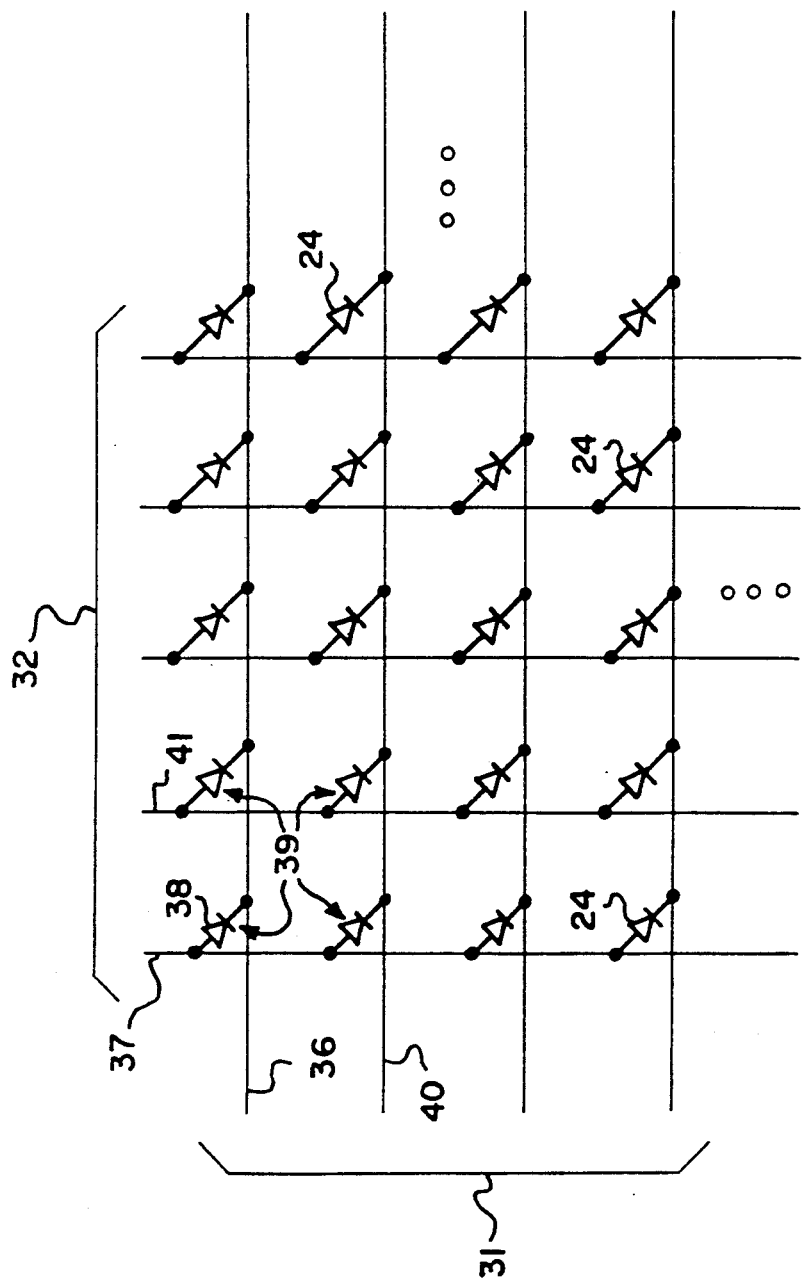
FIG. 4 is a partial schematic illustration of the electrical connections used in controlling the lighting system shown in FIG. 2.

To this end, reference is now made to FIG. 4 of the drawings, which schematically shows the manner in which the array of LED's 24 may be effectively controlled in accordance with the present invention. Illustrated is what essentially constitutes a diode control matrix 30 comprised of addressable electrical connections 31, 32. To be noted is that the electrical connections 31 correspond to the defined latitudes 25 of the lighting fixture 20, while the electrical connections 32 correspond to the defined longitudes 26 of the lighting fixture 20.

Each light emitting diode of the array of LED's 24 is electrically connected between one of the connections 31 and one of the connections 32, in series with a resistor (not shown for clarity of illustration) for equalizing the lighting produced within the array. Each of the series of LED's 24 may then be selectively (individually or in groups) operated by applying appropriate control (biasing) voltages to the electrical connections 31, 32. This has the advantage of permitting any of a variety of lighting patterns to be developed using straight-forward control techniques which do not require the individual activating switches (or relays) which would be necessary for controlling other types of lighting elements.

For example, by suitably addressing the electrical connections 36, 37, a single LED 38 may be operated. A quadrant 39 of LED's may be operated by suitably addressing the electrical connections 36, 37, 40, 41, and so on. Suitably addressing the electrical connection 36 and each of the electrical connections 32 associated with the lighting fixture 20 may be used to operate a selected ring 42 of LED's corresponding to a given latitude 25 of the lighting fixture 20. Other patterns may be developed according to need, and as desired.

Operating selected LED's, or quadrants of LED's, may be used to provide the selected illumination which is desired for inspecting printed circuit boards making use of the techniques disclosed in U.S. patent application Ser. No. 07/159,774. This facilitates the inspection of printed circuit boards during the "pre-solder" and "post-solder" stages of the manufacturing process, as disclosed in this earlier patent application. However, further in accordance with the present invention, the array of LED's 24 (and its facilitated manner of control) has been found to be particularly useful in developing rings of light which can be used to provide inspection functions beyond those disclosed in U.S. patent application Ser. No. 07/159,774, as follows.

Previously, it was common practice to selectively operate the series of cameras 13, 14, 15, 16 to acquire a series of images which could then be used to develop an "intensity map" of the viewing field then under study. While this served to provide a reliable inspection of a printed circuit board, it has been found that this inspection can be still further enhanced by using the lighting fixture 20 of the present invention to develop what is essentially a "topographical map" of the viewing field under inspection. In general, this is accomplished by selectively and preferably sequentially developing rings of light corresponding to the various longitudes 26 defined by the lighting fixture 20. The cameras 13, 14, 15, 16 are then each used to acquire a "series" of images developed by these various rings of light, which can then be suitably stored in memory for subsequent display and analysis as is schematically illustrated in FIG. 5 of the drawings. These images are preferably developed at regular intervals (e.g., every 33 ms) making use of sequential rings of light, preferably of the same intensity, which progress inwardly toward the center of the lighting fixture Referring now to FIG. 5 of the drawings, the element 50 represents what is generally known as the "frame grabber" (storage buffer) of the inspection apparatus 10. Thus, as previously described and further in accordance with the present invention, a series of "bit planes" 51 corresponding to the sequential strobings of rings of light along the longitudes 26 of the lighting fixture 20 are developed within the frame grabber 50, for each of the cameras 13, 14, 15, 16. Each of the bit planes 51 are then "assigned" a color and a level (or weight), for further processing as follows.

For purposes of display, a conventionally available color processing circuit 52 is placed in communication with the frame grabber 50, to assign various colors to the several bit planes 51 developed as previously described. The "colorized" data stored within the frame grabber 50 is then capable of being displayed on a monitor 53, which operates to display a series of colored layers developed responsive to the sequentially strobed rings of light previously described. This, in essence, constitutes a reliefed illustration or three dimensional image corresponding to the viewing field then under inspection since the various colors displayed on the monitor 53 will correspond to images produced (responsive to the strobed rings of light) at different elevations relative to the printed circuit board under inspection. This effect has been found to produce a mapping which constitutes a three dimensional representation of a two dimensional image (on the screen 53), providing a significantly enhanced image for visual inspection purposes.

For purposes of analysis, a processor 54 is also placed in communication with the frame grabber 50. The processor 54 operates to, in essence, assign a level (or weight) to each of the several bit planes 51 defined within the frame grabber 50 as previously described. These weighted values can then be numerically analyzed to determine volumes corresponding to features then under inspection.

Of primary importance here is that this enables the shape of a solder connection (or fillet) to be analyzed even more effectively than was previously possible. For example, by isolating certain layers (defining a "topographical zone") and summing the number of pixels detected within each defined topographical zone, a measure of solder volume can be made. By analyzing the smoothness of the transitions from one topographical zone to the next, a measure of solder wetting can be made (determined primarily by the solder's adhesion to the surface, and generally described by the smoothness of the resulting joint). By detecting aberrations or secondary shapes (measured in similar fashion), voids, blow holes and pinholes may be detected. Thus, significant information may be developed by performing these weighted calculations, making use of the sequential images acquired within the frame grabber 50 in accordance with the present invention.

Further versatility is achieved in accordance with the present invention as a result of the series of four cameras 13, 14, 15, 16 which are available for inspection purposes. This results from the separate generation of acquired images as previously described, by each of the four cameras which are provided. This in turn generates a series of four topographical mappings, from each of four sides of a component under inspection or a completed solder fillet. By correlating (combining or connecting) data stored within the several bit planes 51 developed responsive to operations of the series of cameras 13, 14, 15, 16, an overall "image" can be created in memory which is significantly more complete than the image generated by a single vertical camera. The resulting image can reveal internal surfaces which would be hidden when viewed vertically, which is especially useful in inspecting solder fillets for straight-through hole leads, or when analyzing "J lead" devices (which typically form solder joints which are not visible from above).

It will further be understood that various changes in the details, materials and arrangement of parts which have been herein described and illustrated in order to explain the nature of this invention may be made by those skilled in the art within the principle and scope of the invention as expressed in the following claims.

What is claimed is:

1. An apparatus for inspecting a printed circuit board, and components affixed to said printed circuit board, said components having leads or pins for engaging features of said printed circuit board for soldered connection thereto, said apparatus comprising:
   means for illuminating said printed circuit board and said components; and
   camera means for receiving light reflected from said printed circuit board and said components, and for producing an electrical signal which varies responsive to the reflected light received by said camera means;
   wherein said illuminating means in comprised of a substantially dome-shaped fixture incorporating an array of individually addressable light producing elements defining a plurality of latitudes and longitudes of the dome-shaped fixture, and means for selectively controlling the light producing elements to activate subsets of the light producing elements within the array at intersections of latitudes and longitudes of the dome-shaped fixture.

2. The apparatus of claim 1 wherein said camera means is comprised of four orthogonally disposed cameras associated with said illuminating means.

3. The apparatus of claim 1 wherein said light producing elements are light emitting diodes.

4. The apparatus of claim 1 wherein light emitting diodes grouped along a selected latitude are simultaneously operable to develop a ring of light.

5. The apparatus of claim 4 which further comprises means for sequentially operating light emitting diodes grouped along selected latitudes to develop a series of rings of light.

6. The apparatus of claim 1 wherein light emitting diodes grouped in a selected quadrant are simultaneously operable to develop a directed source of light.

7. The apparatus of claim 1 which further comprises means for acquiring images from said camera means, for storage in a buffer.

8. The apparatus of claim 7 wherein said light producing elements are controllable to develop a plurality of rings of light, and wherein said acquiring means acquires a plurality of images corresponding to said plurality of rings of light.

9. The apparatus of claim 8 wherein said rings of light illuminate different topographical zones associated with said components and said leads or pins.

10. The apparatus of claim 9 wherein said rings of light are sequentially and serially operated.

11. The apparatus of claim 9 wherein said rings of light are operated to produce substantially constant levels of light.

12. The apparatus of claim 9 which further comprises means for assigning colors to said different topographical zones, for display on a color monitor.

13. The apparatus of claim 9 which further comprises means for assigning light levels to said different topographical zones, and for performing weighted and volumetric calculations responsive to said assigned light levels.

14. The apparatus of claim 13 wherein said camera means is comprised of four orthogonally disposed cameras, and wherein said calculation performing means includes means for correlating data stored in said buffer for different ones of said cameras.

15. In an apparatus for inspecting a printed circuit board, and components affixed to said printed circuit board, said components having leads or pins for engaging features of said printed circuit board for soldered connection thereto, said apparatus comprising means for illuminating said printed circuit board and said components, and camera means for receiving light reflected from said printed circuit board and said components, and for producing an electrical signal which varies responsive to the reflected light received by said camera means, an improved illuminating means comprising a substantially dome-shaped fixture incorporating an array of individually addressable light producing elements defining a plurality of latitudes and longitudes of the dome-shaped fixture, and means for selectively controlling the light producing elements to activate subsets of the light-producing elements within the array at intersections of latitudes and longitudes of the dome-shaped fixture.

16. The apparatus of claim 15 wherein said camera means is comprised of four orthogonally disposed cameras associated with said illuminating means.

17. The apparatus of claim 15 wherein said light producing elements are light emitting diodes.

18. The apparatus of claim 15 wherein light emitting diodes grouped along a selected latitude are simultaneously operable to develop a ring of light.

19. The apparatus of claim 18 which further comprises means for sequentially operating light emitting diodes grouped along selected latitudes to develop a series of rings of light.

20. The apparatus of claim 19 wherein said rings of light illuminate different topographical zones associated with said components and said leads or pins.

21. The apparatus of claim 20 wherein said rings of light are sequentially and serially operated 22. The apparatus of claim 20 wherein said rings of light are operated to develop substantially constant levels of 23. The apparatus of claim 15 wherein light emitting diodes grouped in a selected quadrant are simultaneously operable to develop a directed source of light.

24. A method for inspecting a printed circuit board, and components affixed to said printed circuit board, said components having leads or pins for engaging features of said printed circuit board for soldered connection thereto, said method comprising the steps of:
    illuminating said printed circuit board and said components making use of illuminating means including a substantially dome-shaped fixture incorporating an array of individually addressable light producing elements defining plurality of latitudes and longitudes of the dome-shaped fixture;
    selectively controlling the light-producing elements to activate subsets of the light-producing elements within the array at intersections of latitudes and longitudes of the dome-shaped fixture; and
    receiving light reflected from said printed circuit board and said components making use of camera means for producing an electrical signal which varies responsive to the reflected light received by said camera means.

25. The method of claim 24 which further includes developing a ring of light by simultaneously operating light producing elements grouped along a selected latitude 26. The method of claim 25 which further includes sequentially operating light producing elements grouped along selected latitudes to develop a series of rings of light.

27. The method of claim 24 which further includes developing a directed source of light by simultaneously operating light producing elements grouped in a selected quadrant.

28. The method of claim 24, which further includes developing a topographical mapping of said printed circuit board and said components responsive to said electrical signal provided by said camera means.

29. The method of claim 28 which further includes acquiring images from said camera means, and storing said images as data in a buffer.

30. The method of claim 29 which further includes controlling said light producing elements to develop a plurality of rings of light, and acquiring a plurality of images corresponding to said plurality of rings of light.

31. The method of claim 30 wherein said rings of light illuminate different topographical zones associated with said components and said leads or pins.

32. The method of claim 31 wherein said rings of light are sequentially and serially operated.

33. The method of claim 31 wherein said rings of light are operated to develop substantially constant levels of light.

34. The method of claim 31 which further includes assigning colors to said different topographical zones, for display on a color monitor.

35. The method of claim 31 which further includes assigning light levels to said different topographical zones, and performing weighted and volumetric calculations responsive to said assigned light levels.

36. The method of claim 35 wherein said camera means is comprised of four orthogonally disposed cameras, and which further includes correlating data stored in said buffer for different ones of said cameras.

* * * * *